United States Patent [19]

Wolvek et al.

[11] 4,444,186
[45] Apr. 24, 1984

[54] ENVELOPE WRAPPING SYSTEM FOR INTRA-AORTIC BALLOON

[75] Inventors: Sidney Wolvek, Brooklyn, N.Y.; Bruce L. Hanson, Wayne; John J. Lucas, Sparta, both of N.J.

[73] Assignee: Datascope Corporation, Oakland, N.J.

[21] Appl. No.: 273,407

[22] Filed: Jun. 15, 1981

[51] Int. Cl.³ .............................................. A61B 17/12
[52] U.S. Cl. .................................. 128/325; 128/1 D
[58] Field of Search ............... 128/1 D, 246, 344, 325, 128/349 B, DIG. 9; 604/96, 103, 102, 104

[56] References Cited

U.S. PATENT DOCUMENTS 4,246,909  1/1981  Wu et al. ..................... 128/767 X
4,248,236  2/1981  Linder ........................... 128/349 B
4,292,974  10/1981  Fogarty et al. ................. 128/344
4,311,133  1/1982  Robinson ....................... 128/1 D

OTHER PUBLICATIONS

SMEC Newsletter, vol. XVII, SMEC Corp., Cooke, Tenn. 38501.

Primary Examiner—C. Fred Rosenbaum
Assistant Examiner—J. L. Kruter
Attorney, Agent, or Firm—Darby & Darby

[57] ABSTRACT

A wrapping system for an intra-aortic balloon in which a wrapping guide is provided which restrains the proximal end of the envelope from rotating as the distal end is rotated thereby providing a uniform wrap of the envelope from its distal to its proximal end. A wrapping wire is provided for rotating the envelope distal end and the wire extends through at least a part of the catheter to which the envelope is attached. A wrapping knob is coupled to the proximal end of the wrapping wire, whose distal end can be detachably coupled to the distal end of the envelope, and the knob is constructed to permit only a predetermined number of rotations in both wrapping and unwrapping the envelope.

14 Claims, 12 Drawing Figures

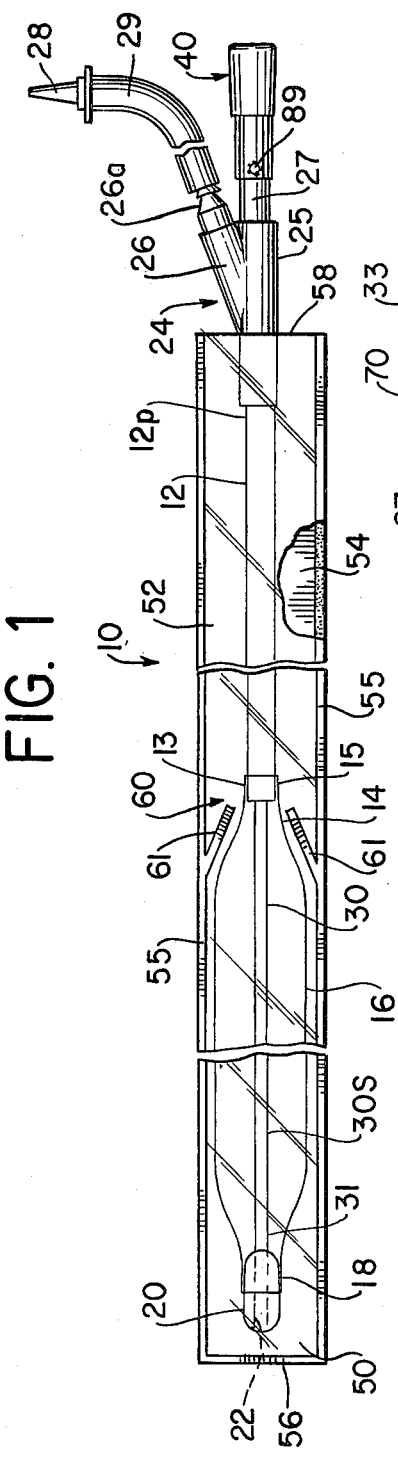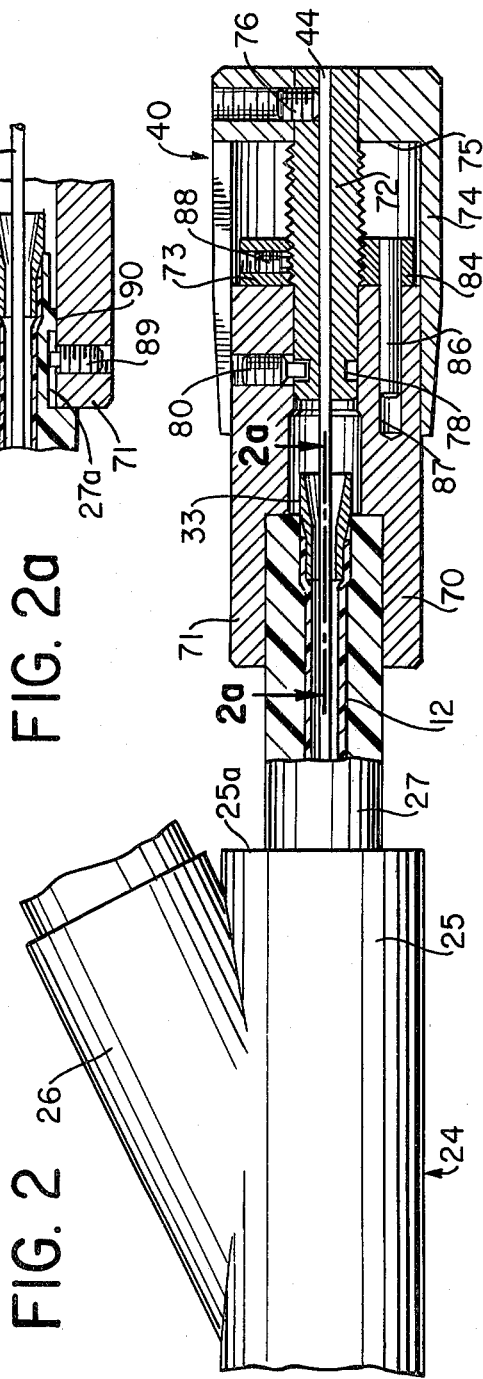

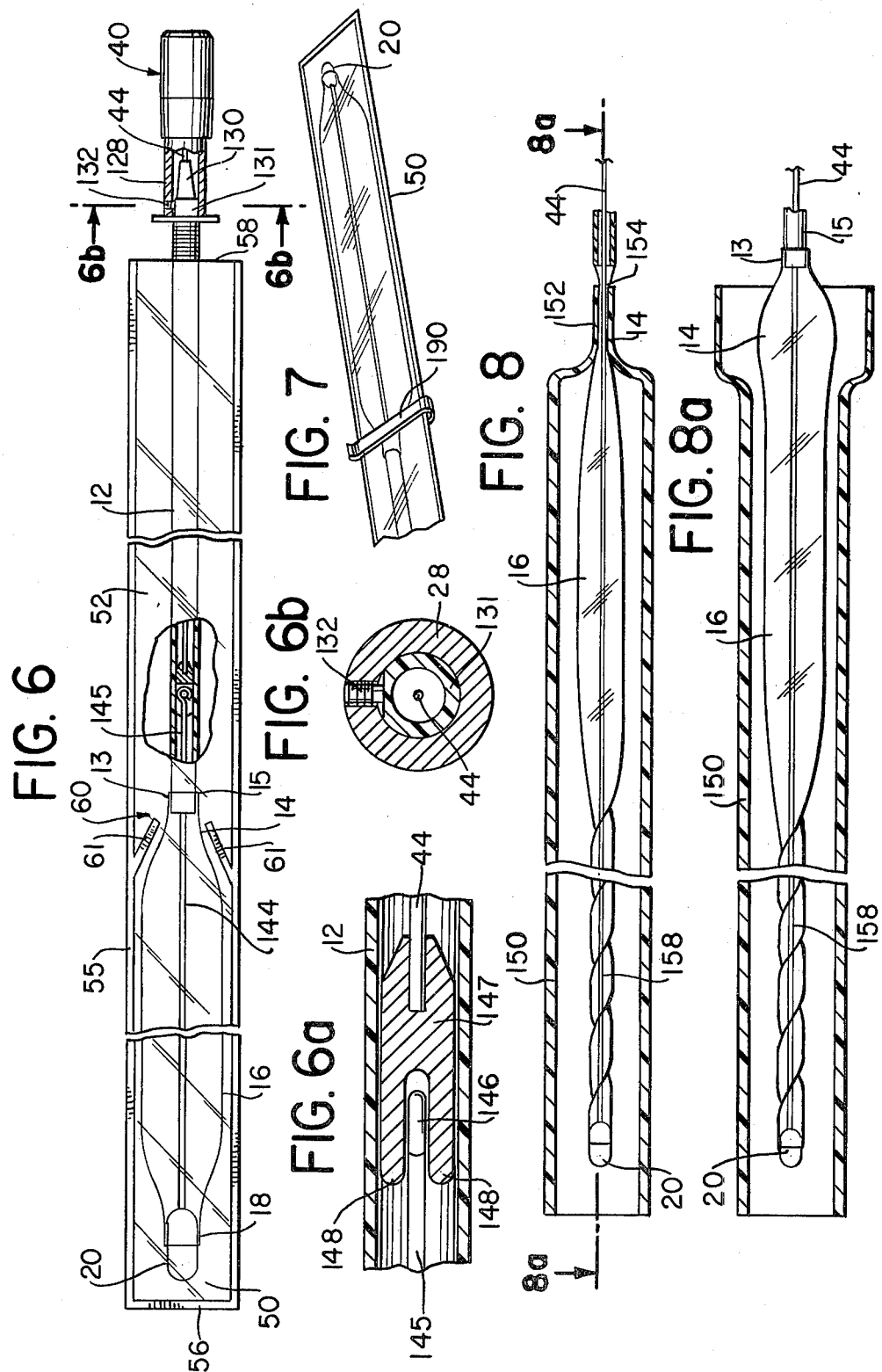

ENVELOPE WRAPPING SYSTEM FOR INTRA-AORTIC BALLOON

Intra-aortic balloons (IAB) are well known. Such balloons comprise a catheter to which is attached one end of a balloon envelope. A support member is located inside of the balloon envelope to support it along its length and to which the other end of the envelope is attached. Gas is supplied through the catheter to the balloon envelope and withdrawn to cause the envelope alternately to inflate and collapse after the envelope has been inserted into the aorta of a human patient.

Several general methods are in use for inserting the balloon into the aorta. One is the usual vascular surgery in which the artery is exposed and the balloon inserted via an incision. More recently, a method of percutaneously inserting such an IAB has been developed in which the balloon is inserted into the patient through a flexible sheath which is passed into an artery of the patient through a suitable puncture made in the patient's skin.

In the percutaneous insertion of an IAB, it is desired to make the diameter of the balloon envelope as small as possible so that the sheath inserted into the artery can also be made as small as possible, thereby increasing the ease with which the IAB can be inserted. One arrangement for decreasing the diameter of the IAB before percutaneous insertion is a so-called balloon envelope wrapping technique in which the envelope is rotated relative to the end of the catheter to which it is attached so that the envelope effectively wraps into a twisted, or spiral form and its diameter is decreased. IAB's which are capable of such wrapping are shown, for example, in U.S. Pat. No. 4,261,339, granted Apr. 14, 1981, and copending application Ser. No. 202,868, both of which are assigned to the same assignee of the subject application.

In the percutaneous insertion of a wrapped balloon envelope, the tightness and uniformity of the wrap is directly related to the ease of insertion into the human body through the smallest possible diameter sheath. In addition, the wrapping should be uniformly accomplished with a number of turns that are evenly spaced over the length of the balloon envelope rather than having all turns localized, or bunched, in one spot. Heretofore, to accomplish this, reliance was principally on the skill of the operator to obtain a uniform wrap and also for the operator to accurately count the number of wraps to prevent an overwrapping which could stress the material. In addition, and quite importantly, the number of turns of the wrap should be known so that when the envelope is unwrapped when inside the artery, the same number of unwrapping turns can be used.

Accordingly, the present invention is directed to an improved wrapping system for an IAB. The system includes a catheter to which is attached a balloon envelope and a support member which extends within the envelope. A wrapping wire which extends through at least a part of the catheter is coupled, preferably removably, to the tip of the balloon envelope at the end opposite the one affixed to the catheter. A wrapper knob is connected to the end of the wire extending from the catheter. The wrapper knob is non-rotatably, but removably, coupled to the catheter. By rotation of the wrapper knob, the envelope can be wrapped relative to the catheter.

The balloon envelope is held within a wrapping guide which is shaped to constrain movement of the end of the envelope adjacent to the catheter. Therefore, when the wrapper knob is rotated, the envelope will wrap starting from its tip toward the juncture of the envelope and the catheter tube. This assures uniform wrapping from the envelope tip to the catheter.

In addition, the wrapper knob is constructed so that a predetermined number of turns of the envelope can be assured both during wrapping and unwrapping. Thus, not only are the wrapping turns uniformly spaced but, also, the number of turns are predetermined. The wrapper knob is also constructed so that the length of the envelope remains unchanged during the wrapping process.

In addition, the wrapper knob is constructed so that it is removable from the catheter immediately after wrapping or unwrapping has been completed in order to make the device extremely flexible for easier insertion into a tortuous artery.

It is therefore an object of the present invention to provide a novel wrapping system for an IAB.

A further object is to provide a wrapping system for an IAB in which the number of wrapping turns of the envelope with respect to the catheter can be predetermined and controlled.

An additional object is to provide a wrapping system for an IAB in which the balloon envelope is located within a wrapping guide which constrains the movement of the portion of the IAB near the juncture of the envelope and the catheter so that the wrapping of the envelope will start from the envelope tip and proceed to the juncture.

A further object is to provide a wrapper knob which can precisely control the number of turns of wrapping and unwrapping of the envelope.

Another object is to provide a wrapping system for an IAB in which a wrapping wire extends through the catheter and is coupled to the tip end of the balloon envelope whose other end is constrained so that the envelope wraps from the tip end as the wire is rotated.

Still another object is to provide a wrapping system which is removable from the intra-aortic balloon prior to the initiation of balloon pumping treatment.

Another object is to provide a wrapping system which does not cause the balloon envelope to change its length during wrapping.

Other objects and advantages of the present invention will become more apparent upon reference to the following specification and annexed drawings in which:

FIG. 1 is an overall plan view of the IAB, the wrapping guide and the wrapper knob as applied to a dual lumen, percutaneously inserted type IAB;

FIG. 2 is an elevational view in section of the wrapper knob;

FIG. 2a is a sectional view of the wrapper knob at the juncture of the fitting of a dual lumen IAB taken along lines 2a—2a of FIG. 2;

FIG. 6 is an overall plan view of an embodiment of the invention for use with a percutaneously inserted IAB of the single lumen type;

FIG. 6a is a fragmentary view in cross section of the coupling of the wrapping wire to the envelope support member;

FIG. 6b is a cross-section of the wrapping knob taken along lines 6b—6b of FIG. 6;

FIG. 7 is a perspective view of a further embodiment of the wrapping guide; and

FIGS. 8 and 8a are elevational views, with FIG. 8a being rotated by 90° from FIG. 8, of a further embodiment of the wrapping guide.

Figure 3:
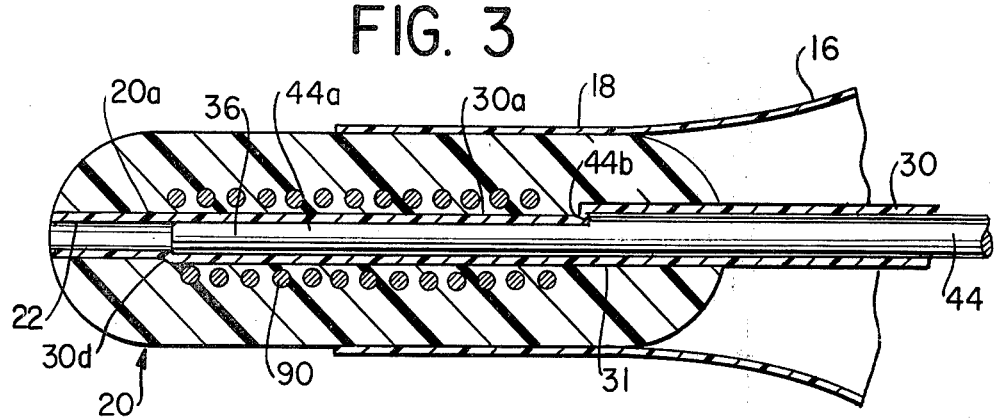
FIGS. 3, 4 and 5 are each a fragmentary view, partly in section of the end of an envelope showing various coupling arrangements for the wrapping wire.

In the following specification the terms "distal" and "proximal" are referenced from the site of the person using the device.

Referring to FIG. 1, there is shown an overall view of an IAB 10 of the so-called double lumen type. The IAB includes an outer lumen, or catheter, 12 which has a distal end 13 to which is attached the proximal end 14 of an elongated balloon envelope 16 of a suitable expansible, but substantially inelastic, material, for example, polyurethane. Catheter 12 is flexible and can be, for example, of polyurethane. The attachment of the envelope to the catheter is accomplished, for example, by use of an adhesive or by heat sealing to form an air-tight seal. There is communication from the distal exit end of catheter 12 into the envelope 16. The other (distal) end 18 of the envelope is sealed to a tip 20 of plastic or other suitable material which has a through bore 22. The tip 20 has a rounded distal end and is discussed in greater detail in FIGS. 3–5.

A Y fitting 24, also of a suitable plastic material, is connected to the proximal end 12p of the outer lumen 12. One branch leg 26 of the Y fitting 24 has a barbed connector 26a to which is attached an intermediate section of tubing 29. A luer connector 28 is attached to the opposite end of tubing 29. The gas inflation mechanism, e.g. a pump (not shown), is attached to the luer fitting 28 to alternately inflate and deflate balloon envelope 16 by inserting and removing gas from the interior of the envelope through the open end of the outer lumen 12 which has free communication with the entire interior of the envelope 16 at the point where the inner lumen passes therethrough.

An inner lumen 30, which can be of the same material as catheter 12, extends through the straight leg section 25 of the Y fitting 26 and into the catheter 12 toward the envelope 16. The inner lumen extending through the length of the balloon envelope 16 and the envelope portion is designated 30s, since it forms the support member for the envelope. The distal end 31 of the inner lumen 30 is attached within the through bore 22 of tip 20, opening to the exterior of the tip. The proximal end of inner lumen 30 terminates in a female luer fitting 33 permanently affixed within an extension 27 of the main leg 25 of the Y-fitting 24.

As discussed below, the extension 27 of the Y-fitting 24 is constructed to cooperate with a wrapper knob 40 whose details are also described below. Fixedly attached to the wrapper knob is a wrapping wire 44 which extends through the interior of the hollow inner lumen and has its end 46 attached to the envelope tip 20 in a non-rotatable, but preferably in a removable, manner (see FIGS. 3–5). The wrapping wire is, for example, of stainless steel. While the term wire is used, it should be understood that the wire can be rod-like.

The majority of the length of the IAB is shown as being located within a wrapping guide 50. This guide 50 can be in the form of a package having front and rear pieces 52 and 54. The rear piece 54 can be, for example, white opaque surgical grade paper to which is heat sealed or sealed by an adhesive around three sides the front piece 52 which is, for example, of transparent low density polyethylene. This permits complete visualization of the components therein and particularly the envelope 16. As seen, the two pieces 52 and 54 are connected around both of the elongated edges 55 and the narrow edge 56 adjacent to the tip of the IAB. The opposite end 58 is left open.

A stricture 60 is formed in the wrapping guide 50, also by heat sealing or otherwise attaching the two sheets 52, 54. The stricture 60 is formed at the narrowed down area of the proximal end 14 of the envelope 16 by two sealed areas 61 angled in from the sides of the package 50.

The IAB 10 is shipped in the form shown in FIG. 1 with the balloon envelope 16 being substantially flat. When it is desired to wrap the envelope relative to the catheter, and thereby reduce its diameter so that it can be percutaneously inserted, this is preferably done immediately prior to the operation that is being performed. To accomplish this, the operator grasps the wrapper knob 40 and begins to rotate it while holding with the other hand the wrapping guide at that portion that overlaps the Y fitting 24. As the knob is rotated, it rotates the wrapping wire 44 whose end 36 (see FIGS. 3 and 4) is coupled to the tip 20 of the envelope. Thus, wrapping of the balloon commences from the distal end 18 since the proximal end 14 of the envelope is constrained from turning by the stricture 60. The wrapping is illustrated in FIG. 8 although a different package is shown. This arrangement ensures that wrapping commences from the distal end of the envelope 16.

If wrapping is permitted starting at the proximal end 14 of the envelope, then the wraps will form a seal preventing air from escaping from the balloon envelope 16 into the catheter passage between the inner and outer lumens 30 and 12. Air will then become trapped in the balloon envelope preventing a tight and complete wrap. In this case, total wrapping would be limited to the proximal neck 14 of the envelope resulting in a possible over-stressing of the envelope at this point. In accordance with the invention, by assuring that wrapping of the envelope begins at the tip, this guarantees proper wrapping of the envelope without over-stressing of the neck.

As seen, the wrapping guide 50 also has a narrow width as compared with the unwrapped width of the envelope. This prevents the forming of an arch of the wrapping wire during wrapping. In addition, the wrapping guide extends over the entire length of the envelope and provides a protected environment for it from the time of the opening of the sterile outer package (not shown) in which the IAB system 10 is shipped to the time of actual balloon insertion. The wrapping guide 50 is removed from the balloon immediately prior to insertion into the patient. This is easily accomplished since the balloon has been wrapped and can easily slip out the neck of the stricture 60 by pulling on the catheter and holding the wrapping guide 50.

After the IAB is percutaneously inserted, the guide wire 44 is removed by pulling the wrapper knob 40 off of extension leg 27 of Y-fitting 24. At this time, the end 36 of the wrapping wire 44 disengages from the tip 20 of the IAB which is constructed to permit this.

FIG. 3 shows one embodiment of a tip 20, and distal end 18 of the envelope and the manner of coupling the wrapping wire 44. In this embodiment, the inner lumen 30, which is of a flexible plastic material is molded into the tip 20 which is of thermoplastic material. During molding, the end portion 30a in end portion 20a of tip 20 has been molded as a flattened, half-round keyway. The distal end 44a of the wrapping wire 44 is also formed, such as by grinding, into a half-round section 44a. This enables the distal end of the wrapping wire 44 to be non-rotatably coupled with the flattened keyway in the tip.

Insertion of the wrapping wire 44 into the tip is limited by a shoulder 44b of the guide wire engaging a shoulder 30b of the inner lumen and the distal end of the guide wire 44 engaging the shoulder 30d of the reduced diameter section 30c of the inner lumen which is molded into the tip. The wrapping wire 44 is thus prevented from passing completely beyond the tip.

To make the tip of the balloon visible in the human body under fluoroscopy after the wrapping wire 44 has been removed, a radiopaque member, such as a stainless steel spring 90, has been molded into the tip 20.

When the wrapping wire 44 is withdrawn, there will be a passage through the inner lumen 30 which extends through the length of the envelope and through bore 22 of tip 20, and also through the fitting 24 via female luer fitting 31. This provides a passage for a safety guide, instrumentation for the acquisition of body measurements, such as blood pressure, injection of radiographic dyes, etc. after the envelope has been unwrapped and the wrapping wire and guide have been removed.

Figure 4:
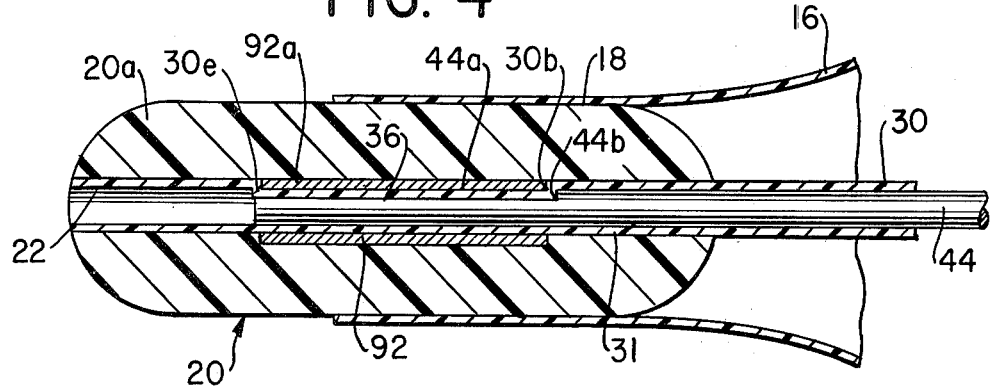

FIG. 4 shows a further embodiment of a key means between the wrapping wire 44 and the tip 20. In this embodiment, an insert piece 92 of a rigid material, such as stainless steel, is placed over the inner lumen 30 prior to molding of the tip 20. The metal piece 92 has a flattened upper section 92a smaller than the inside diameter of the inner lumen 30. Thus, that section of the inner lumen is compressed within the insert piece 92 to assume a new cross-sectional shape corresponding to a flattened keyway.

As in the case of FIG. 3, the distal end of the wrapping wire 44 is formed with a flattened section 44a having a shoulder 44b. The wrapping wire 44 is prevented from passing completely through the tip by the shoulder 44b of the wrapping wire engaging the shoulder 30b of the inner lumen 30 which is formed by the compressive action of the metal insert piece 92. The insert piece is prevented from being pushed through the tip by the wire by a shoulder 30e of the inner lumen 30 acting against the edge of the insert piece 92. In an alternate form, the insert piece is tubular with a flattened central section and is placed fully within inner lumen 30 with the tip thereafter being molded over the inner lumen. The flattened section 44a of the wire passes through the flattened central section to provide keying and the shoulder 44b provides the stop.

In this embodiment a radiopaque member, such as the spring 90 of FIG. 3, is not necessary since the metal insert 92 forms its own radiopaque shadow under fluoroscopy. As also in the case of FIG. 3, there is a passage through the entire length of the inner lumen 30 for various uses.

Figure 5:
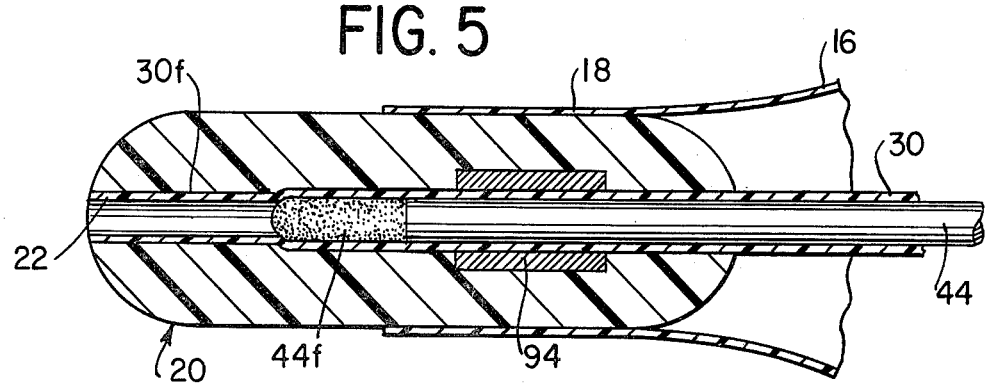

FIG. 5 shows a further embodiment of keying between the tip 20 and the wrapping wire 44. In this case, the inner lumen 30 has a reduced diameter end section 30f within the tip near the distal end. The diameter of the reduced section 30f is smaller than that of the wrapping wire 44 and this may be typically in the range of about 0.005 inches less than that of the diameter of the wire which is typically approximately 0.040 inches.

In FIG. 5, the distal end 40f of the wrapping wire may be treated, for example by sandblasting, to provide a textured surface. Thus, the engagement of the rounded end 44f of the wrapping wire 44 provides engagement with the inner lumen 30 and through the tip 20 so that the rotation of the envelope on the distal end can take place as previously described.

A piece of stainless steel 94 or other suitable material is molded into the tip 20 to provide the fluoroscopic visibility of the tip in the human body after the wrapping wire 44 has been removed.

In using the embodiment of FIG. 5, a slight push on the wrapping wire, for example approximately 3 pounds, forces the rounded tip 44f of the wrapping wire to enter into reduced diameter section 30f of the tip. The compressible nature of the tip 20 material, such as polyurethane, allows the soft plastic wall of inner lumen 30 to distend outwardly to allow the rounded tip to enter the reduced diameter lumen area 30f. The end 44f of the wrapping wire 44 continues to enter the reduced diameter lumen area 30f for a short distance, for example 0.125 inches, until the compressive force of the material of the tip reacting against the increased length of the inserted wire tip 44 prevents further insertion of the wrapping wire. This compressive force against the textured end 44f of wrapping wire 44 effectively keys the wire to permit the rotational torque applied to the wrapping wire 44 by the wrapping knob 40 to be effectively transmitted to the tip of the balloon, thereby effecting envelope wrapping.

Removal of the wrapping wire 44 is accomplished by pulling on the wrapping knob with a force equal to that used in inserting the wrapping wire into the reduced diameter area of tip 20.

The details of the wrapping knob 40 are shown in FIGS. 2 and 2a. As seen, the proximal end of the wrapping wire 44 passes through an inner housing 70, an elongated outside threaded member 72 and an outer housing 74. A set screw 76 at the end of the outer housing locks this housing, threaded member 72 and the wrapping wire 44 together.

The end 71 of the inner housing 70 closest to the Y-fitting 24 is non-rotatably engaged with a flat 27a of the Y-fitting extension 27. A circumferential groove 78 is provided around the end of the threaded member 72 which extends into the inner housing 70 and a set screw 80 which is threaded in the inner housing and has a tip of nylon or other suitable material which rides in this groove. Thus, rotation of the outer housing 74 will rotate the threaded member 72 by virtue of the rotatable coupling provided by set screw 80.

A traveling nut 84 is threaded onto the threaded member 72. Nut 84 has a guide rod 86 attached to it which is in turn inserted in a hole 87 in the inner housing 70 so that the nut 84 is restrained from rotating relative to the inner housing but can move longitudinally to it.

In operation, as the outer housing 74 of the knob 40 is rotated, for example clockwise, or in the right hand direction, the traveling nut 84 travels toward the right, as shown in FIG. 2, until it is stopped by coming into contact with the end wall 75 of the outer housing 74. The guide rod 86 allows nut 84 to travel longitudinally on threaded member 72 by preventing the nut from rotating as rotation of outer housing 74 turns the threaded member 72 relative to the inner housing 70. Longitudinal movement of the threaded member 72 is prevented by the screw 80 riding in the circumferential groove 78.

It should be understood that the number of wraps permitted by the wrapper knob as it is turned clockwise can be limited by the traveling nut. The nut first abuts the end wall 73 of the inner housing 70, then will allow rotation of the outer housing 74 until the nut moves along the threaded member 72 and is stopped by the inner surface of the end wall 75 of the outer housing 74. This will cause the envelope to be wrapped for a number of turns as permitted by the distance of travel of nut 84 and the number of rotations of the outer housing 74.

Rotation of the outer housing 74 in a counterclockwise, or left hand direction, will continue until the traveling nut is once again stopped at its starting point against the wall 73 of inner housing 70. This causes unwrapping of the envelope. Complete unwrapping of the envelope takes place in the body of the patient and there is no overshoot, that is unwrapping of more turns than the number of turns wrapped. In addition, it will be seen that rotation of the wrapping knob 40 cannot result in a lengthening or a shortening of the balloon under the action of the wrapping wire since the threaded member 72 to which the end of the wrapping wire 44 is rigidly connected does not move longitudinally with rotation, but, instead, the traveling nut 84 does.

A set screw 88, of nylon or other similar material, is placed through the traveling nut 74 and bears against the threaded member 72. Set screw 88 is adjusted during assembly to provide sufficient rotational resistance to prevent accumulated torque of the wrapped balloon envelope from rotating threaded member 72 after the envelope 16 has been wrapped.

As seen in FIGS. 2 and 2a, the wrapping knob 40 is removably attached to the extension 27 of the fitting 24 by a set screw 89 on the end 71 of the inner housing 70 of the wrapping knob 40 which slips over the extension 27 of the Y-fitting 24 in which the inner lumen 30 becomes accessible. The set screw 89 engages a flat 27a on one surface of fitting extension 27.

The set screw 89 provides non-rotatable alignment between the wrapper knob 40 and the Y-fitting and provides a drag fit against flat 27a on the extension 27 of the Y-fitting. Inadvertent removal of the wrapping knob from the balloon is prevented by the resistance of a detent 90 extending from flat 27a against the tip of the set screw 89. However, a deliberate pull on the inner housing 70 will cause screw 89 to disengage over the detent 90.

If re-engagement of the knob with the IAB is required, as the wrapper knob inner housing 70 passes over the proximal end of flat 27a of the Y-extension 27, the distal end the wrapping wire 44 enters into coupling engagement with the tip 20, to be discussed below with respect to FIGS. 3–5. This assures the simultaneous re-keying or re-insertion of the wire within tip 20 and that of the knob 40 to the fitting 24. When the distal end of the inner housing 70 abuts the shoulder 25a on the Y-fitting extension 27 (see FIG. 2a) the wrapping wire is completely keyed or coupled with the tip 20.

During assembly of the IAB, the key section 44a of the wrapping wire 44, the keyway 30a of tip 20 as seen in FIG. 3 and flat 27a of extension 27 are aligned by the action of the set screw 76 on the threaded member 72.

Due to the use of the travelling nut arrangement, a rotation of the wrapping knob 40 and the wrapping wire does not cause any elongation or contraction of the length of the wire relative to the envelope. Therefore, the length of the envelope is kept constant.

FIGS. 6, 6a and 6b show an embodiment of a single lumen IAB utilizing the wrapping system. Here, a support member 144, which can be a wire, or metal or plastic rod, tube, or strip, is provided for the envelope 16. The support member 144 has its distal end coupled, and preferably fixed, to the tip 20. This can be accomplished by molding, adhesive, heat sealing etc. The proximal end 145 of the support member 144 extends into the catheter for a distance where it is coupled to the wrapping wire 44.

The wrapper knob is similar to that of FIGS. 2, 2a. It has an inner housing 128 which is non-rotatably secured to a male leur fitting 130 at the end of the catheter 12 and through which the wrapper wire 44 passes. This is done by a set screw 132 engaging a flat 134 on a boss 131 of the leur fitting.

The distal end of the wrapping wire is connected to and terminates in a fork 147 having tines 148. Fork 147 can be made of stainless steel or other similar material and is permanently affixed, such as by welding or soldering to the distal end of wire 44. The space between the tines 148 is wide enough to admit and hold a hooked end 146 of the rotatable support member 144.

Rotation of the outer housing 40 of the knob, as described in connection with FIGS. 2 and 2a, is transmitted to the support member 144 by the wrapping wire 44 and fork 147. The wrapping of the envelope occurs in the manner previously described from the distal toward the proximal end of the envelope.

Upon completion of the envelope wrapping operation, the wrapping knob 40 can be removed from the luer fitting 130 by a pulling action making the fitting available for connection with the balloon pumping means.

The wrapping guide for the embodiment of FIG. 6 is similar to that shown and described in connection with FIG. 1 for the restraining of the envelope, or in accordance with any of the embodiments of FIGS. 2 and 8.

FIG. 7 shows another embodiment of the invention in which the wrapping guide 50 is of a somewhat different configuration from that previously disclosed. Instead of using the sealing areas 61 to restrain the rotation of the envelope, a clip 190, which can be a spring clip of metal, plastic or other similar material, is placed across the wrapping guide package 50 in the narrowed down area of the proximal end 14 of the envelope. The IAB can be either of the single or double lumen type. By rotation of the wrapping wire in accordance with any of the previous embodiments, the proximal end of the balloon envelope is restrained from rotating and the wrapping of the balloon will proceed from the distal end of the envelope as previously described.

FIGS. 8 and 8a show a further embodiment of the wrapping guide. In this embodiment, the guide 150 is generally tubular in shape and is formed of a suitably rigid material having a low degree of surface friction such as, for example, low density polyethylene. Other suitable plastic materials also can be utilized.

As seen, one end 152, of the wrapping guide 150 is flattened, for example by thermoforming or the like, so that a restricted opening 154 is formed. The walls of the flattened end of 152 have been reduced or thinned by the action of thermoforming from their original dimensions and that of the remainder of the wall of the wrapping guide 150 so that they are rendered more flexible. The proximal end of the envelope 14 resides in this narrow slit like opening 154 formed by the thinned-walled portion of the guide.

In using the embodiment of FIGS. 8–8a, either a single or double lumen IAB can be contained therein. Rotation of the wrapping wire 44 is transmitted to the balloon envelope tip 20 as the wire continues to be rotated. The action of the wall 152 of the narrow space 154 on the envelope end 14 retards wrapping of that end of the envelope so that wrapping is initiated at the distal tip 20 end of the balloon as indicated by wraps 158 in FIG. 8a.

As wrapping continues, the entire balloon is eventually wrapped up to the end of the catheter. At that time, wrapping guide 150 is removed from the wrapped envelope by pulling the guide over the tip 20, or toward the left as shown in FIGS. 8-8a. The thin relatively flexible walls 152 defining the opening 154 deflect so that the wrapped envelope and the remainder of the balloon can be easily removed from the wrapping guide.

In the preferred embodiments of the invention described, the wrapping wire is removble from the IAB. It should be understood that the wrapping guides are also usable with single or multi-lumen IABs in which the wrapping wire is not removable, for example, it is fixed to the tip, or to the inner lumen, or to the support member. In this case, the wrapping guide still serves its previously described function of making the wrapping start from the distal end of the envelope when the wrapping wire is rotated.

What is claimed is:

1. A wrapping system for an intra-aortic balloon comprising:
   a balloon assembly including a hollow catheter and an elongated envelope having its proximal end connected to said catheter,
   a member coupled to the distal end of said envelope and extending through it to support the envelope along its length,
   means coupled to the distal end of said envelope and extending through it to support the envelope along its length,
   means coupled to said distal end of said envelope for rotating said distal end, and
   a housing in which said envelope is located, said housing having means for restraining the proximal end of said envelope as the distal end is rotated to cause wrapping of the envelope relative to the catheter to proceed from the distal end of the envelope toward the proximal end.

2. A system as in claim 1 wherein said housing comprises a package having front and rear sheets of material which are attached and between which said envelope is placed, and said restraining means comprising a portion of said sheets which are attached together in at least one area adjacent the proximal end of said envelope.

3. A system as in claim 1 whereas said housing comprises a package having front and rear sheets of material which are attached and between which said envelope is placed, and said restraining means comprising clip means on the outer surface of said sheets.

4. A system as in claim 1 wherein said housing comprises a tubular member in which said envelope is located, a portion of said tubular member being formed to engage and restrain the proximal portion of said envelope.

5. A system as in claim 4 wherein said portion of said housing has resilient walls which permit the wrapped balloon to be moved therethrough.

6. A system as in claim 1, wherein said support member comprises a lumen which extends the length of said envelope, said lumen having its distal end fastened to said envelope distal end and its proximal end extending within said catheter, a removable wrapping wire passing through said lumen and coupled to the distal end of said envelope for rotating it, withdrawal of said wire from said lumen providing a through passage from said lumen proximal end through the distal end and external of said envelope.

7. A system as in claim 6 further comprising a tip piece which forms a part of said wire coupling means to which the distal end of said lumen is attached, said tip piece also having a through passage.

8. A wrapping system as in claim 1 wherein said member for supporting said envelope is hollow and has its distal end attached to the distal end of said envelope, said means for rotating said distal end of said envelope comprising a wrapping wire extending within said hollow support member.

9. A system as in claim 8 further comprising means for rotating said wire comprising an inner housing, means coupling said inner housing to said proximal end of said wrapping wire, an outer housing rotatable relative to inner housing, a threaded member within said outer housing and fixed to rotate therewith, and a nut traveling on said threaded member as said outer housing is rotated and which is movable along said threaded member between said inner and outer housings.

10. A system as in claim 9 wherein the length of the threaded member determines the number of predetermined turns by the abutment of said nut with said inner and outer housings.

11. A wrapping system as in claim 8 wherein said envelope further comprises a tip piece attached to its distal end, the distal end of said hollow support member attached to said tip piece, and means for coupling the distal end of said wrapping wire to said envelope tip piece.

12. A system as in claim 11 wherein said means for coupling the distal end of said wrapping wire to said tip piece includes means for detachably coupling the wire to the tip.

13. A system as in claim 12 wherein said means for detachably coupling the distal end of said wrapping wire to said tip comprises mating key means formed on said tip and said wire.

14. A system as in claim 12 wherein said means for detachably coupling the distal end of said wrapping wire to said tip comprises a force fit between the distal end of said wire and said tip.

* * * * *